United States Patent [19]
Saito et al.

[11] Patent Number: 6,020,898
[45] Date of Patent: Feb. 1, 2000

[54] INFORMATION DISPLAY SYSTEM FOR DISPLAYING TIME-SERIES NUMERICAL VALUES AND GRAPH SIMULTANEOUSLY

[75] Inventors: Akito Saito, Hino; Toshio Horiguchi, Hachioji, both of Japan

[73] Assignee: Olympus Optical Co., Ltd., Tokyo, Japan

[21] Appl. No.: 08/089,433

[22] Filed: Jul. 12, 1993

[30] Foreign Application Priority Data

Jul. 27, 1992 [JP] Japan ................................. 4-199840
Sep. 28, 1992 [JP] Japan ................................. 4-258557

[51] Int. Cl.[7] ................................................. G06F 15/00
[52] U.S. Cl. ................................................. 345/440
[58] Field of Search ............................... 395/140, 141, 395/142; 345/440, 123, 124, 125, 133, 134, 333, 334

[56] References Cited

U.S. PATENT DOCUMENTS

| | | | |
|---|---|---|---|
| 4,455,609 | 6/1984 | Inamura et al. | 364/414 |
| 5,247,611 | 9/1993 | Norden-Paul et al. | 395/161 |
| 5,261,031 | 11/1993 | Saito | 395/140 |

*Primary Examiner*—Phu K. Nguyen
*Attorney, Agent, or Firm*—Armstrong, Westerman, Hattori, McLeland & Naughton

[57] ABSTRACT

Information recorded on optical recording media is reproduced by a recording/reproducing unit. A plurality of predetermined items are selected by a keyboard among reproduced information. A list of inspection data of time-series order in which all inspection data of a plurality of selected items are in the time-series order, and a list in which numerical-value data of the selected items are graphed in time-series order are simultaneously displayed on the same display surface.

22 Claims, 17 Drawing Sheets

FIG.1 (PRIOR ART)

| INSPECTION DATE | 1982 | 1983 | 1984 | 1985 | 1986 | 1987 | 1988 | 1989 | 1990 | 1991 |
|---|---|---|---|---|---|---|---|---|---|---|
| | 10.10 | 10.10 | 10.10 | 10.10 | 10.10 | 10.10 | 10.10 | 10.10 | 10.10 | 10.10 |
| HEIGHT | 167.4 | 167.4 | 167.4 | 167.2 | 167.5 | 167.4 | 167.2 | 168.2 | 167.5 | 168.0 |
| WEIGHT | 55.0 | 57.0 | 59.0 | 60.5 | 65.0 | 68.5 | 69.5 | 71.5 | 70.2 | 74.0 |
| DEGREE OF CORPULENGE | 87 | 90 | 93 | 96 | 103 | 108 | 110 | 112 | 111 | 116 |
| MAXIMUM BLOOD PRESSURE | 120 | 124 | 130 | 130 | 130 | 118 | 144 | 128 | 132 | 132 |
| MINIMUM BLOOD PRESSURE | 60 | 62 | 72 | 80 | 90 | 84 | 98 | 100 | 90 | 95 |
| URINE PROTEIN | − | − | − | − | − | − | − | − | − | ± |
| URINE OCCULT BLOOD | − | − | − | − | − | − | − | − | − | − |
| URINE SUGAR | − | − | − | − | − | − | − | ± | + | ++ |
| NUMBER OF ERYTHROCYTES | 452 | 455 | 465 | 469 | 452 | 455 | 474 | 465 | 471 | 443 |
| Hb | 14.3 | 14.5 | 14.8 | 14.8 | 14.3 | 14.5 | 15.1 | 14.8 | 15.5 | 14.0 |
| Ht | 44.0 | 43.1 | 47.0 | 42.4 | 44.0 | 43.1 | 45.0 | 47.0 | 43.6 | 42.0 |
| MCV | 95 | 95 | 97 | 96 | 95 | 95 | 95 | 97 | 93 | 94 |
| NUMBER OF LEUCOCYTES | 9100 | 7800 | 9700 | 7300 | 9100 | 7800 | 9900 | 6700 | 6800 | 7100 |
| GOT | 44 | 42 | 46 | 50 | 48 | 40 | 42 | 30 | 47 | 22 |

FIG.8

| SECT. m | INSP. DATE (1) | 1 | VAL.OF HEIGHT (1) | 2 | VAL.OF WEIGHT (1) | - - - | SECT. n | INSP. DATE (2) | 1 | VAL.OF HEIGHT (2) | 2 | VAL.OF WEIGHT (2) | - - - |

FIG.9

| INSP. DATE (1) | 1 | VAL.OF HEIGHT (1) | 2 | VAL.OF WEIGHT (1) | - - - | INSP. DATE (2) | 1 | VAL.OF HEIGHT (2) | 2 | - - - |

FIG.10

PLEASE SELECT DISPLAY ITEMS {A}

{SIMPLE ITEM}

| | | | | | URIC ACID | 31 | |
|---|---|---|---|---|---|---|---|
| 1 | HEIGHT | 11 | Ht | 21 | STOOL OCCULT BLOOD | 32 | |
| 2 | WEIGHT | 12 | MCV | 22 | | 33 | |
| 3 | DEGREE OF CORPULENCE | 13 | NUMBER OF LEUCOCYTES | 23 | | 34 | |
| 4 | MAXIMUM BLOOD PRESSURE | 14 | GOT | 24 | | 35 | |
| 5 | MINIMUM BLOOD PRESSURE | 15 | GPT | 25 | | 36 | |
| 6 | URINE PROTEIN | 16 | LDH | 26 | | 37 | |
| 7 | URINE OCCULT BLOOD | 17 | ALP | 27 | | 38 | |
| 8 | URINE SUGAR | 18 | γ-GTP | 28 | | 39 | |
| 9 | NUMBER OF ERYTHROCYTES | 19 | BLOOD SUGAR | 29 | | 40 | |
| 10 | Hb | 20 | AMY | 30 | | | |

{GROUP}

| A | 1,2,3,8 |
|---|---|
| B | 14,15,18 |
| C | 4,5,6 |
| D | |
| E | |
| F | |
| G | |
| H | |
| I | |
| J | |

| INSP. DATE | 1982 10.10 | 1983 10.10 | 1984 10.10 |
|---|---|---|---|
| VAL.OF HEIGHT | 167.4 | 167.4 | 167.4 |
| VAL.OF WEIGHT | 55.0 | 57.0 | 59.0 |
| DEG.OF CORPUL. | 87 | 90 | 93 |
| URINE SUGAR | — | — | — |

FIG.13

| INSPEC. DATE | 1982 10.10 | 1983 10.10 | 1984 10.10 | 1985 10.10 | 1986 10.10 | 1987 10.10 | 1988 10.10 | 1989 10.10 | 1990 10.10 | 1991 10.10 |
|---|---|---|---|---|---|---|---|---|---|---|
| VAL.OF HEIGHT | 167.4 | 167.4 | 167.4 | 167.2 | 167.5 | 167.4 | 167.2 | 168.2 | 167.5 | 168.0 |
| VAL.OF WEIGHT | 55.0 | 57.0 | 59.0 | 60.5 | 65.0 | 68.5 | 69.5 | 71.5 | 70.2 | 74.0 |
| DEG.OF CORPUL. | 87 | 90 | 93 | 96 | 103 | 108 | 110 | 112 | 111 | 116 |
| URINE SUGAR | − | − | − | − | − | − | − | −+ | + | ++ |

FIG.20

PLEASE SELECT DISPLAY ITEMS [3,6,7,8]

CAPABLE OF SELECTING FOUR ITEMS TO THE MAXIMUM

| 1 | HEIGHT | 11 | Ht | 21 | URIC ACID | 31 | |
|---|---|---|---|---|---|---|---|
| 2 | WEIGHT | 12 | MCV | 22 | STOOL OCCULT BLOOD | 32 | |
| 3 | DEGREE OF CORPULENCE | 13 | NUMBER OF LEUCOCYTES | 23 | | 33 | |
| 4 | MAXIMUM BLOOD PRESSURE | 14 | GOT | 24 | | 34 | |
| 5 | MINIMUM BLOOD PRESSURE | 15 | GPT | 25 | | 35 | |
| 6 | URINE PROTEIN | 16 | LDH | 26 | | 36 | |
| 7 | URINE OCCULT BLOOD | 17 | ALP | 27 | | 37 | |
| 8 | URINE SUGAR | 18 | γGTP | 28 | | 38 | |
| 9 | NUMBER OF ERYTHROCYTES | 19 | BLOOD SUGAR | 29 | | 39 | |
| 10 | Hb | 20 | AMY | 30 | | 40 | |

INFORMATION DISPLAY SYSTEM FOR DISPLAYING TIME-SERIES NUMERICAL VALUES AND GRAPH SIMULTANEOUSLY

BACKGROUND OF THE INVENTION

1. Field of the Invention

The present invention relates to an information display system for simultaneously displaying contents of items selected among reproduced information by time-series numerical values and a graph.

2. Description of Related Art

Conventionally, various information recording media such as optical or photo cards, magnetic tapes, magnetic disks, photo disks, and photo-electro-magnetic disks are used for recording information. In recent years, various kinds of data bases have been formed, and bulk information has been stored. For example, in the field of health art, a data base for storing therein the results of a medical examination performed periodically by a self-governing community is formed. The stored personal information has been used for various kinds of statistical totalization processing, and health guidance due to doctors and health nurses with respect to residents or inhabitants.

Conventionally, these data bases have been used with an organization which manages health information in a lump, such as, for example, a municipal office and a health center, and have been recorded onto information recording media relatively large or high in memory capacity such as magnetic tapes, magnetic disks, optical disks and photo-electro-magnetic disks. However, as far as a network due to on-line covering a wide area or field is not full-equipped, the stored Information cannot be utilized, if an organization in which the information is stored is not utilized.

For this reason, information recording media provided both with sufficient recording capacity and superior portability for recording of information corresponding to one person, such as, for example, the optical card is used, information for each individual is recorded onto these media, and each individual carries the media, whereby a system capable of effectively utilizing the information in a plurality of organizations has been put to practical use.

The information stored in the optical card is displayed by processing the past results of consultation and is used as a reference for guidance of heal th of a consulted person due to doctors and health nurses.

FIG. 1 of the attached drawings is a drawing ex ample in which inspection data corresponding to ten (10) inspections recorded onto an optic al card by a prior art device are arranged and displayed such that inspection items are arranged in a line direction, and a list in which the inspection data for each inspection date are arranged in a column direction is displayed. Thus, it is possible to see time-series variation of a plurality of inspection data only with an image plane by this list.

Further, FIG. 2 is a drawing example in which the inspection data corresponding to ten (10) inspections is displayed on a broken line graph in a time-series manner with inspection dates expressed along the abscissa and with inspection items expressed along the ordinate axis. If the inspection data produced by numerical-value data are expressed by a broken line graph in a time-series manner, it is possible to grasp variation or change in the inspection data in a visual-sense manner.

However, in the broken line graph shown in FIG. 2, it is possible to grasp the variation of the inspection data of a single item in a visual-sense manner. Since, however, it is impossible to simultaneously display the inspection data of a plurality of inspection items, it is difficult to grasp the mutual relationship between the associated inspection items. On the other hand, in the list shown in FIG. 1, a plurality of items can be displayed simultaneously. However, it is impossible to grasp the variation of the inspection data in a visual-sense manner. Accordingly, in order to know the variation in the plurality of inspection data and the relationship between the plurality of inspection data in a visual-sense manner, an operation is required such that graph display every inspection items is printed out onto a sheet of paper and these papers are superimposed upon each other. There is a problem that it is difficult to use.

Moreover, in the broken line graph illustrated in FIG. 2, it is possible to grasp the variation of the inspection data in a visual-sense manner. However, it is impossible to read only rough or general values of the inspection data from the graph. Accordingly, in order to know exact numerical values of the inspection data, it is required that graph display is suspended, and the list shown in FIG. 1 is displayed. Thus, there is a problem that operability is unsatisfactory or undesirable.

SUMMARY OF THE INVENTION

It is an object of the invention to provide an information display system capable allowing the operator to, in a visual-sense manner, grasp variation in inspection data of a plurality of inspection items by a simple operation in which exact numerical values of various inspection items are conveyed without a change of image planes or picture planes.

It is an another object of the invention to provide an information display system capable of displaying inspection information in a form in which a doctor easily performs health guidance of a person consulted by a physician.

According to the invention, there is provided an information display system comprising:

reproducing or playback means for reproducing information extending over a plurality of items recorded on information recording media;

selecting means for selecting combined item groups grouped into a plurality of predetermined combinations of items from among information extending over the plurality of items reproduced by the reproducing means;

time-series order numerical-value data generating means belonging to the combined item groups selected by the selecting means, for generating time-series order numerical-value data in which numerical-value data are arranged in time-series order, with respect to items including the numerical-value data;

time-series order graph generating means for generating a time-series order graph in which the numerical-value data are brought to the graph of time-series order, with respect to items including the numerical-value data; and display means for simultaneously displaying the time-series order numerical-value data and the time-series order graph.

Accordingly, since the numerical-value data and the graph of the plurality of predetermined items are displayed within the same image plane, it is possible both to grasp exact data of the items and to grasp, in a visual-sense manner, time-series variation of the items by simple operation.

BRIEF DESCRIPTION OF THE DRAWINGS

FIG. 1 is a view for explanation, showing an example of a list displayed in a prior art;

FIGS. 3 to 16 relate to a first embodiment of the invention, FIG. 3 being a block diagram showing an entire arrangement of an information display system according to the first embodiment of the invention;

FIG. 4 is a view for explanation of a schematic structure of an optical card;

FIG. 5 is a schematic arrangement view showing an optical-card reader/writer;

FIG. 6 is a block diagram showing an arrangement of the information display system according to the first embodiment of the invention;

FIG. 7 is a flow chart showing processing contents of the first embodiment;

FIG. 8 is a view for explanation, showing recording contents of inspection data recorded onto the optical card;

FIG. 9 is a view for explanation, showing reproducing data which are stored in a reproducing-data storing area of a RAM;

FIG. 10 is a view for explanation, showing an example of a menu image plane which selects displayed items;

FIG. 11 is a view for explanation, showing data after the data of the selected items are rearranged in time-series order;

FIG. 12 is a view for explanation, showing a list of data rearranged in time-series order;

FIG. 13 is a view for explanation, showing a list of data displayed on an display;

FIG. 14 is a view for explanation, showing image data of a time-series graph stored in a RAM in time series;

FIG. 15 is a view for explanation, showing the fact that image data of the table and image data of a graph are stored respectively in a pair of frame memories;

FIG. 16 is a view for explanation, showing the fact that the list and the graph are simultaneously displayed on an display;

FIG. 18 is a flow chart showing a principal portion of operation contents in the second embodiment;

FIGS. 19 to 21 relate to a third embodiment of the invention, FIG. 19 being a flow chart showing a principal portion of operation contents in the third embodiment;

FIG. 20 is a view for explanation, showing an example of a menu image plane which selects a displayed item; and FIG. 21 is a view for explanation, showing the fact that a list and a graph are simultaneously displayed on an display.

DETAILED DESCRIPTION OF THE PREFERRED EMBODIMENTS

Hereunder, various embodiments of the invention will successively be described with reference to the accompanying drawings.

Figure 2:
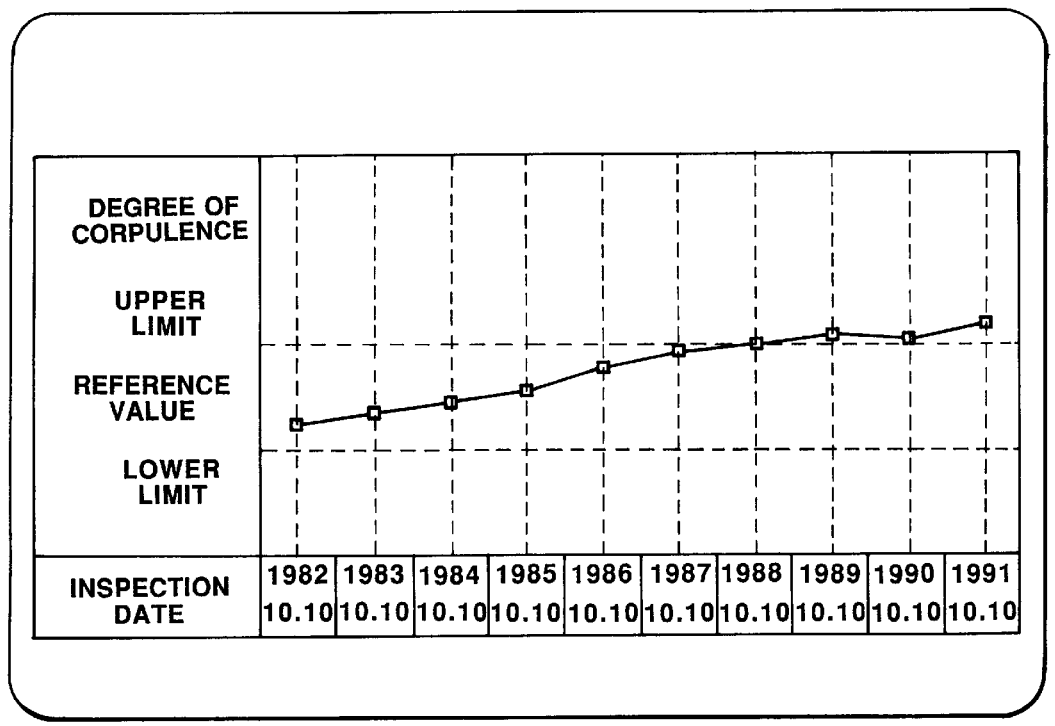
FIG. 2 is a view for explanation, showing an example of a graph displayed in the prior art.
Figure 3:
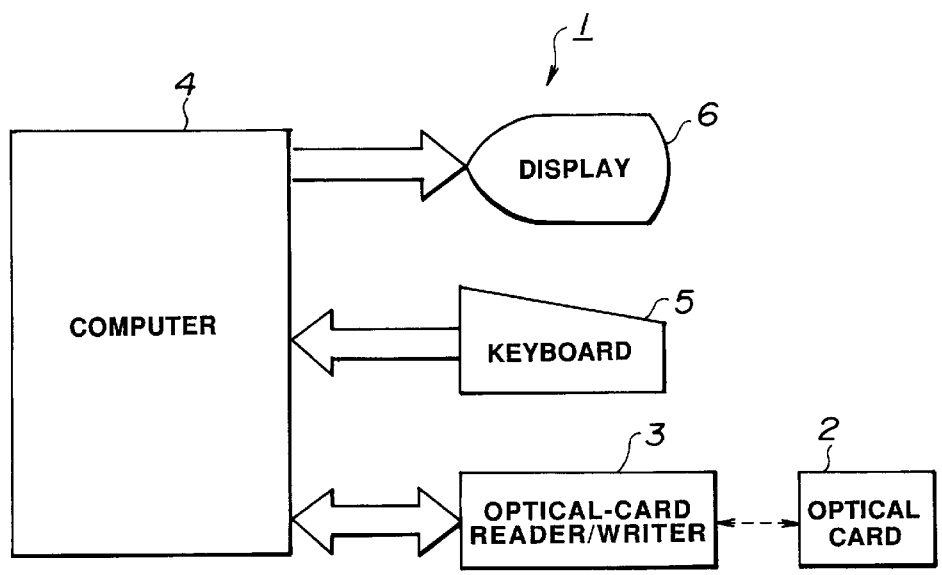

An information display system 1 according to a first embodiment of the invention illustrated in FIG. 3 comprises an optical-card reader/writer 3 provided with a function of recording information onto an optical card 2 serving as an optical recording medium and a function of reproducing the recorded information, a computer 4 connected to the optical card reader/writer 3 for indicating recording/reproducing of the information and for performing processing outputting information reproduced by the optical-card reader/writer 3 as time-series data, processing for graphing the information in time series in a case where the time-series data are numerical-value data, and the like, a keyboard 5 connected to the computer 4, for inputting information giving indication of items displayed with respect to the computer 4, and a display 6 connected to the computer 4 and serving as an output unit, for displaying an output from the computer 4.

The display 6 has a function of displaying contents of inspection data outputted from the computer 4 and contents in which numerical-value data of the inspection data are graphed in time series, all on the same image plane.

Figure 4:
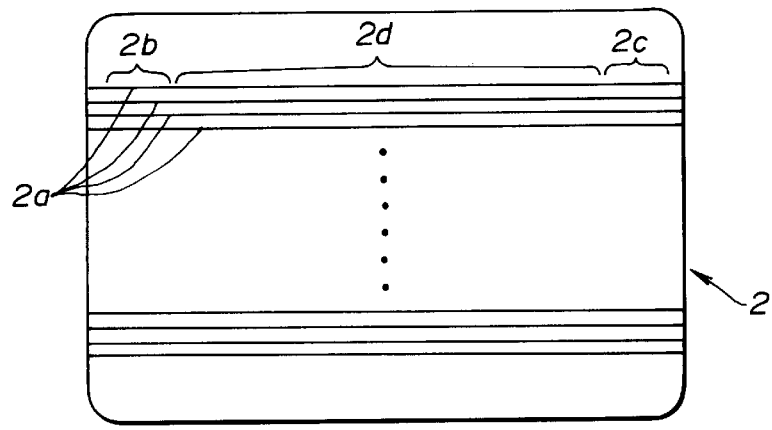

As shown in FIG. 4, the optical card 2 is formed with a plurality of tracks 2a in a longitudinal direction. Each of the tracks 2a has both ends thereof which are provided with ID sections 2b and 2c on which track numbers of the track 2a are recorded. A data section 2d on which information is optically recorded is formed between the ID sections 2b and 2c.

Further, each track is divided into a plurality of sectors so that information is recorded in a sector unit.

Figure 5:
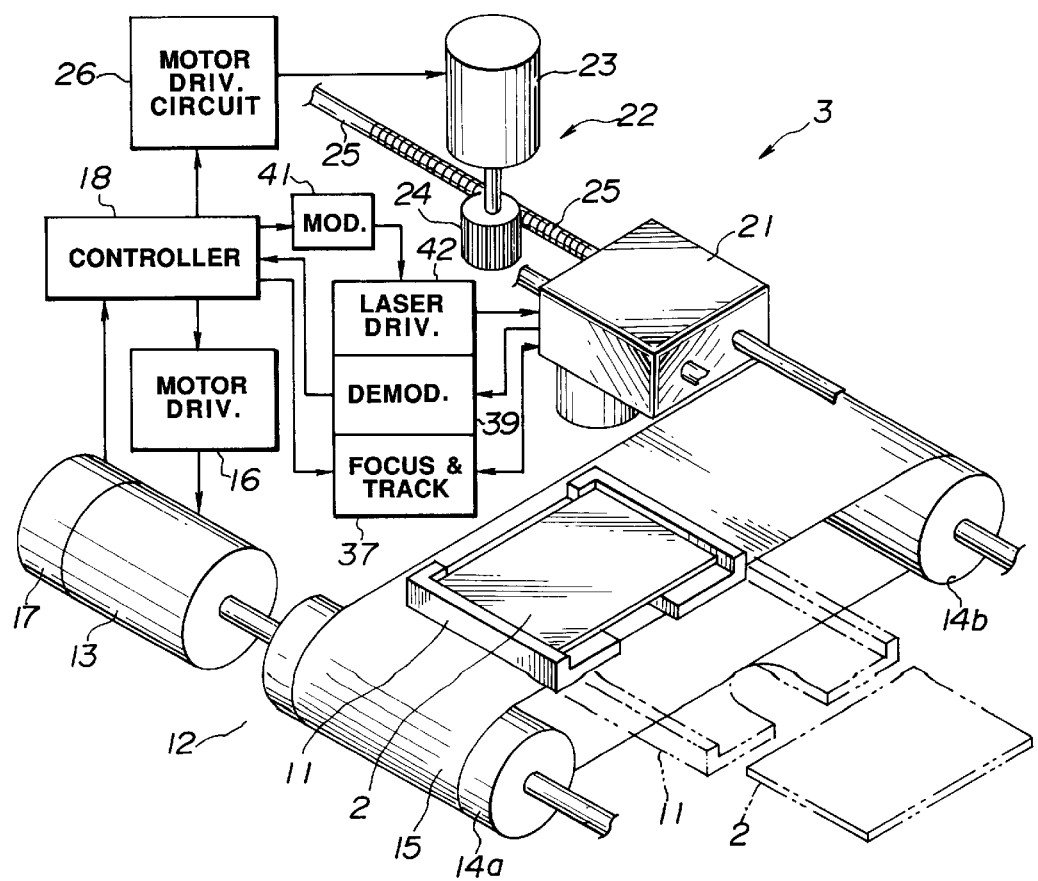
Figure 6:
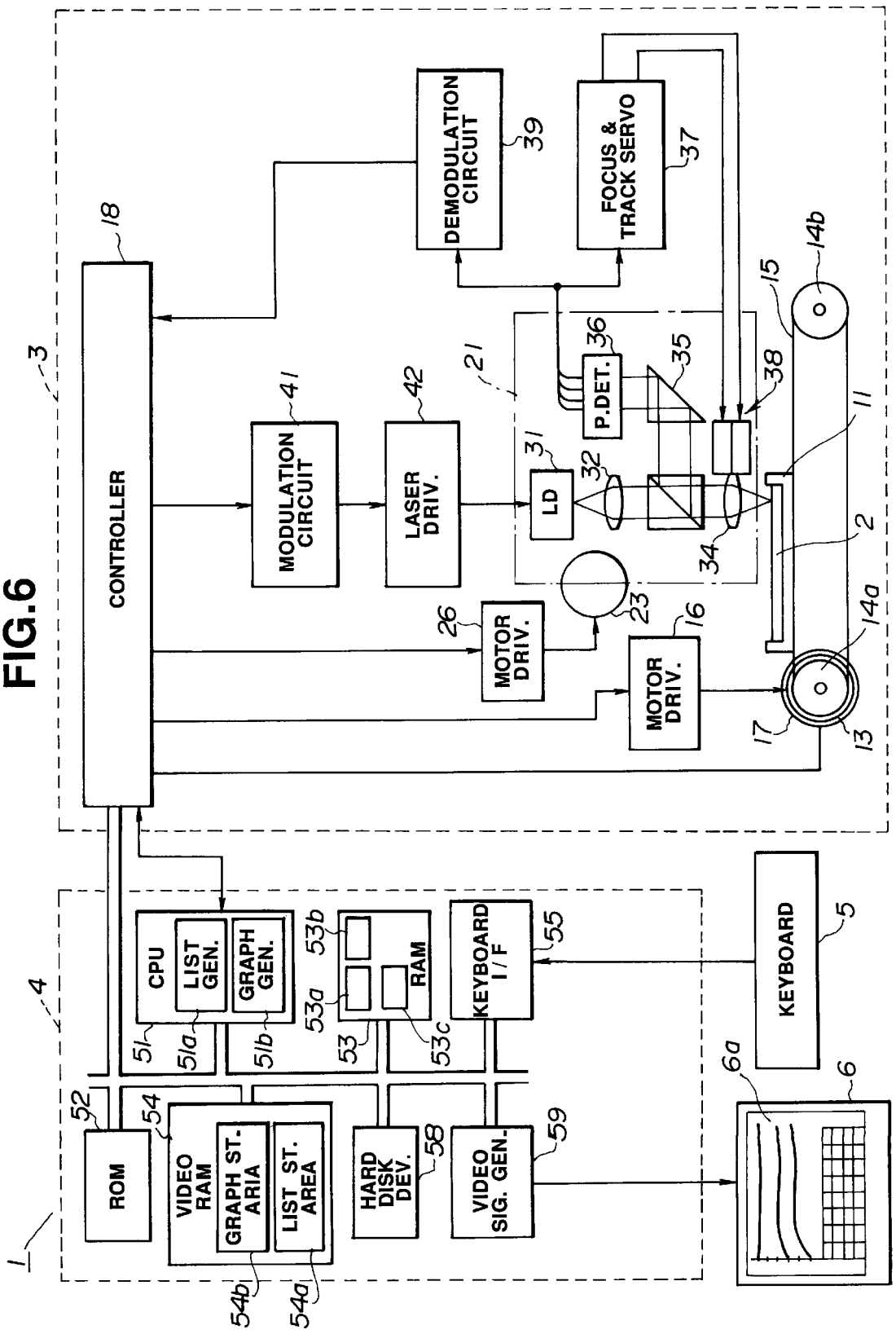

The optical-card reader/writer 3 provided with function of recording the information onto the optical card 2 and function of reproducing the recorded information is arranged as shown in FIGS. 5 and 6.

In the optical-card reader/writer 3 shown in FIG. 5, the optical card 2 inserted through an inserting opening and indicated by a two-dot-and-chain line is mounted on an optical-card holding table 11 by a loading mechanism (not shown), is carried together with the optical-card holding table 11, and rests at a predetermined mounting position where recording/reproducing is performed, in an optical-card feed mechanism 12.

The optical-card feed mechanism 12 comprises a driving motor 13, one of rollers 14a mounted on a rotary shaft of the driving motor 13 and the other roller 14b arranged in spaced relation to the roller 14a, and a belt 15 passed between these rollers 14a and 14b. A positive drive signal for rotating the motor 13 in a clockwise direction is applied through a motor drive circuit 16, whereby the optical card 2 is carried together with the optical-card holding table 11 to the right in a horizontal direction.

Moreover, a negative drive signal is applied to the motor 13, whereby the optical card 2 is carried to the left in the horizontal direction, together with the optical-card holding table 11. An amount of carrying the optical card 2 is detected by a rotary encoder 17 which is mounted on the rotary shaft of the motor 13.

A direction in which the optical card 2 is carried is in parallel to the longitudinal direction of the optical card 2. Accordingly, the direction in which the optical card 2 is carried is in parallel to a direction in which the track 2a extends (referred to as "a track direction").

The optical-card feed mechanism 12 is controlled by a controller 18.

An optical head 21 is arranged in opposed relation to the optical card 2 which rests on the optical-card feed mechanism 12. The optical head 21 is movable in a track crossing direction which extends perpendicularly to the track direction, by a head feed mechanism 22. The optical head 21 is moved in the track crossing direction by the head feed mechanism 22, whereby it is possible to have access to an optional track.

The head feed mechanism 22 comprises a driving motor 23, a gear 24 mounted on a rotary shaft of the driving motor 23, and a shaft 25 which is formed with a threaded portion 25a in mesh with the gear 24 and on which the optical head 21 is mounted. The motor 23 is supplied with positive and negative drive signals from a motor drive circuit 26 to move the optical head 21 in directions opposite to each other in response to the positive and negative drive signals. The head feed mechanism 22 is also controlled by the controller 18.

As shown in FIG. 6, a laser diode 31 is accommodated within the optical head 21. Light radiated by the laser diode 31 is condensed by a collimator lens 32 so as to be brought to a parallel optical beam. The optical beam is incident upon a beam splitter 33. Transparent light thereof is condensed by an objective lens 34, and is incident upon the optical card 2, to thereby form minute beam spots on a minute area portion on the optical card 2.

Light reflected from the minute area portion is condensed by the objective lens 34, and is incident upon the beam splitter 33. Light reflected by the beam splitter 33 is received by an optical detector 36 through a critical-angle prism 35. The optical detector 36 is formed by, for example, four-divided optical detecting elements, so that a focus error signal and a track error signal are generated by each pair of difference signals. Furthermore, information recorded by a pit array is reproduced by a sum signal of four (4) optical detecting elements.

An output signal from the optical detector 36 is inputted to a focus & track servo circuit 37 so that a focus servo signal and a track servo signal are generated. The focus servo signal and the track servo signal are applied to a lens actuator 38. The objective lens 34 is controlled in movement to an optical-axis direction by the focus servo signal, to perform controlling such that a beam spot formed on the optical card 2 is brought to a focus condition.

Moreover, the objective lens 34 is controlled in movement to the track crossing direction by the track servo signal to perform controlling such that the beam spot formed on the track 2a of the optical card 2 is brought to a tracking condition which maintains a central portion (in a widthwise direction) of the track 2a.

Furthermore, an output signal from the optical detector 26 is inputted to a demodulation circuit 39 and is demodulated to generate a reproducing signal. The reproducing signal is transmitted toward the computer 4 through the controller 18.

Further, when a signal to be recorded is transmitted from the computer 4 to the controller 18, the controller 18 causes an error correction code to be added to the signal and, thereafter, modulates the signal by a modulation circuit 41. The signal passes through a laser-diode drive circuit 42 to control a light emitting power of the laser diode 31. A pit array is formed on the track 2a of the optical card 2 in accordance with the light emitting power of the laser diode 31 so that the controller 18 performs recording of information. In a case of a playback or reproducing mode, the light emitting power of the laser diode 31 is maintained at a low constant or predetermined level.

The computer 4 which performs transmittance of the information with respect to the optical-card reader/writer 3 comprises, as shown in FIG. 6, a CPU 51 for performing entire control and having a list generating function 51a for generating a list of data in time-series order and a graph generating function 51b for generating a graph of numerical-value data in time-series order, a ROM 52 which is connected to the CPU 51 through a bus and to which characters or the like are written, a RAM 53 into which data are temporarily stored and which is used in data processing, a video RAM 54 for storing therein image data displayed on a monitor 6a serving as the display 6, a keyboard interface 55 connected to the keyboard 5, a hard disk device 58 in which an OS program for setting operation environment operating the CPU 51, an application program for displaying inspection data under the OS, and the like are recorded, and a video-signal generating circuit 59 for generating an image signal which is displayed on the monitor 6a.

The CPU 51 is connected to the controller 18 of the optical-card reader/writer 3 through a control signal line so that a signal can be sent between the CPU 51 and the controller 18. Further, the controller 18 is connected to the bus so that reproduced data can be transmitted toward the computer 4, and data recorded onto the optical card 2 can be transmitted toward the side of the controller 18 from the side of the computer 4.

Operation of the present embodiment will hereunder be described with reference to a flow chart in FIG. 7.

A power source of the system 1 is turned ON, whereby the computer 4 and the optical-card reader/writer 3 are brought to an operative condition. That is, the computer 4 reads the OS program from the hard disk device 56, so that an application program for displaying inspection data is activated under the read OS. The CPU 51 reproduces personal information of the optical card 2 with respect to the controller 18 of the optical-card reader/writer 3, in a case where the optical card 2 is inserted, and indicates that the personal information is transmitted toward the computer 4.

Accordingly, the optical-card reader/writer 3 is brought to a waiting condition waiting that the optical card 2 is inserted.

First, as shown in a step SI, the optical card 2 of a user who wants to display the inspection data is inserted into the optical-card reader/writer 3. Then, as shown in a step S2, the optical-card reader/writer 3 reproduces the personal information (such as the name, the date of birth, a sex distinction, an ID and the like) which is written onto the inserted optical card 2. The personal information such as the name, the date of birth, the sex distinction, the ID and the like is recorded on the data section in which the track number is 1, for example.

As shown in a step S3, the optical-card reader/writer 3 transmits the reproduced personal information to the computer 4.

The computer 4 displays the transmitted personal information on the display 6 (step S4). Display is performed which requires confirmation or affirmation as to whether the personal information displayed on the display 6 is the same as that of the person in question (step S5). Here, if the personal information displayed on the display 6 is not the same as that of the person in question, N or NO is inputted to the keyboard 5. Then, a program proceeds to a step S16 where the optical card 2 is emitted, and processing ends.

On the other hand, if the personal information displayed on the display 6 is the same as the person in question, an operator inputs Y or YES by the keyboard 5. In this case, since the CPU 51 judges that the personal information displayed on the display 6 is the same as the person in question, the program proceeds to a step S6 where the optical-card reader/writer 3 reproduces all the inspection data recorded on the optical card 2.

The inspection data recorded on the optical card 2 are sequentially recorded such as, for example, an inspecting date on which inspection is performed, on a leading portion of a data section of a sector m, subsequently, the inspection item number 1 expressing that an inspection item is a height, subsequently an inspection item number 2 expressing as being a measured value of the height and the weight, subsequently a measured value of the weight . . . , and an end mark is recorded after the last inspection data of the inspection item, as shown in FIG. 8. In this connection, in FIG. 8, for example, INSP.DATE (1) indicates that the date is the oldest date (in this embodiment, INSP.DATE (1) expresses Oct. 10, 1982), and (2) indicates that the date is the second one.

In a case where inspection is next performed, an inspection date on which inspection is performed, the inspection item number 1, a measured value of the height, the inspection item number 2, and a measured value of the weight . . . in order from the leading portion of the data portion of a subsequent sector n (in a case where a sector is only one at the previous inspection data, n=m+1) of the sector used in the previous inspection data are recorded similarly to the previous inspection data.

These inspection data are all reproduced by the optical-card reader/writer 3, and are transmitted to the computer 4 as indicated by a step S7.

The inspection data transmitted to the computer 4 are temporarily stored as shown, for example, in FIG. 9 in a reproducing-data storing area 53a within the RAM 53 under the control of the CPU 51. That is, the inspection date, the inspection item number 1, the measured value of the height . . . are stored in the reproducing-data storing area 53a with the sector number removed in FIG. 8.

The CPU 51 performs display of all the items, as shown, for example, in FIG. 10, which requires selection of the display items as to which or what items should be displayed in a case where the inspection data are displayed (step S8).

That is, it is required for the operator as to which one of the fact that two lists including a list of the inspection item number indicated by a group and a list of the inspection item number every one are displayed on the display image plane of the display 6 so that display of a plurality of inspection items are performed simultaneously. An optional one inspecting item (hereinafter referred as "simple item") is displayed is detected. Further, a list of the simple items are simultaneously displayed together with the inspection item corresponding to the inspection item number, and the operator understands what combinations of the inspecting items are with respect to display of combinations of the inspection item numbers indicated by the groups.

The grouped "groups" are that simple items are combined with a plurality of previously associated item groups and are grouped such that desirable item groups can be selected.

For example, "group A" indicated by an identification code A is that four (4) inspection items including the height, the weight, a degree of corpulence and urine sugar are beforehand combined with each other. Similarly, "group B" is that three (3) items including GOT, GPT and γ-GTP are beforehand combined with each other, and "group C" is that three (3) items including the maximum blood pressure, the minimum blood pressure and urine protein are beforehand combined with each other.

The combination item information indicating which inspection item belongs to every groups is transmitted to a combination item storing area 53b within the RAM 53 from the hard disk device 58 in a case where the application program is activated, for example. The inspection items within the group are displayed with the item number on the display 6 under the control of the CPU 51 as shown in FIG. 10. When "group" is selected, the CPU 51 detects that a plurality of corresponding items belonging to the group are selected, and performs an operation which displays the information with respect to the plurality of items in time series.

The operator selects the inspection items desired to be displayed, that is, the display items desired to be displayed on the display 6 by the keyboard 5 as indicated by a step S9.

In an example of an image plane as shown in FIG. 10, "A" is inputted as an identification code of the inspection item, indicating a condition where "group A" (a set of the height, the weight, the degree of corpulence and the urine sugar) is selected. Then, the CPU 51 extracts data of the height, the weight, the degree of corpulence and the urine sugar corresponding respectively to the item numbers 1, 2, 3 and 8 of the height, the weight, the degree of corpulence and the urine sugar from data (illustrated in FIG. 9) within the reproducing-data storing area 53a in the RAM 53. The data of the height, the weight, the degree of corpulence and the urine sugar are rearranged to data of the order of time series as shown in a step S10 so as to be brought to time-series order data which are stored in a time-series order data storing area 53c of the RAM 53.

Figures 11, 12:
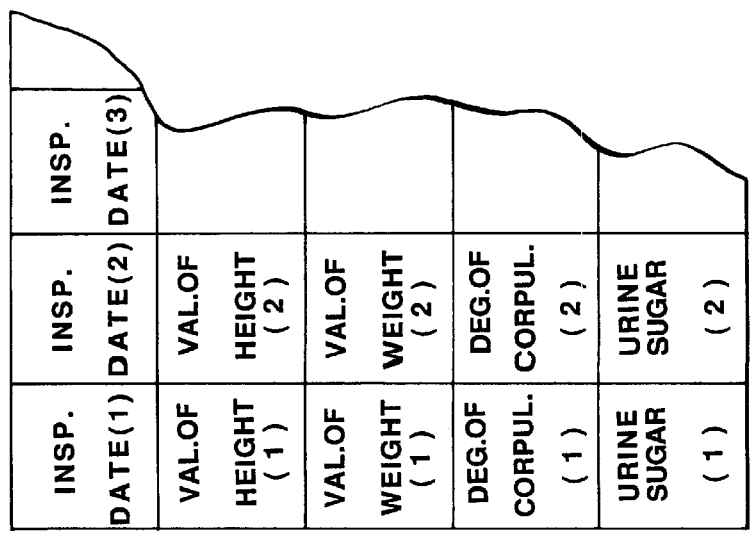

The time-series order data are brought, by the CPU 51, to time-series order data in which data of the height, the weight, the degree of corpulence and the urine sugar are arranged in old inspection date order as shown, for example, in FIG. 11, and are stored in the time-series order data storing area 53c.

Subsequently, a list of the time-series order data is generated by the fact that ruled lines are drawn into the time-series order data, as indicated by a step S11, and is stored in a list storing area 54a of the video RAM 54.

Image data of the list of the bit images are stored in the list storing area 54a of the video RAM 54, as illustrated in FIG. 12, for example.

The image data of the list of the time-series order data stored in the video RAM 54 are converted to a standard image signal by the video-signal generating circuit 59. The standard image signal is outputted to the display 6 as indicated by a step 12, and a list is displayed on the display surface 6a as shown in FIG. 13.

The list shown in FIG. 13 is the same as the bit image shown in FIG. 12, which is stored in the video RAM 54. As shown in FIG. 13, an upper side of the display surface 6a of the display 6 is blanked, and is subsequently secured as a display area of the time-series graph.

Moreover, the CPU 5 judges at a step S13 whether or not the data of the display item are numerical-value data. As indicated in a step S14, in a case where the data of the display item are the numerical-value data, the time-series numerical-value data are graphed to perform processing in which a time-series graph is generated.

The time-series graph is stored, as image data, in a graph storing area 54b of the video RAM 54. Subsequently, the image data of the time-series graph are outputted to the display 6 as indicated in a step S15.

Figure 14:
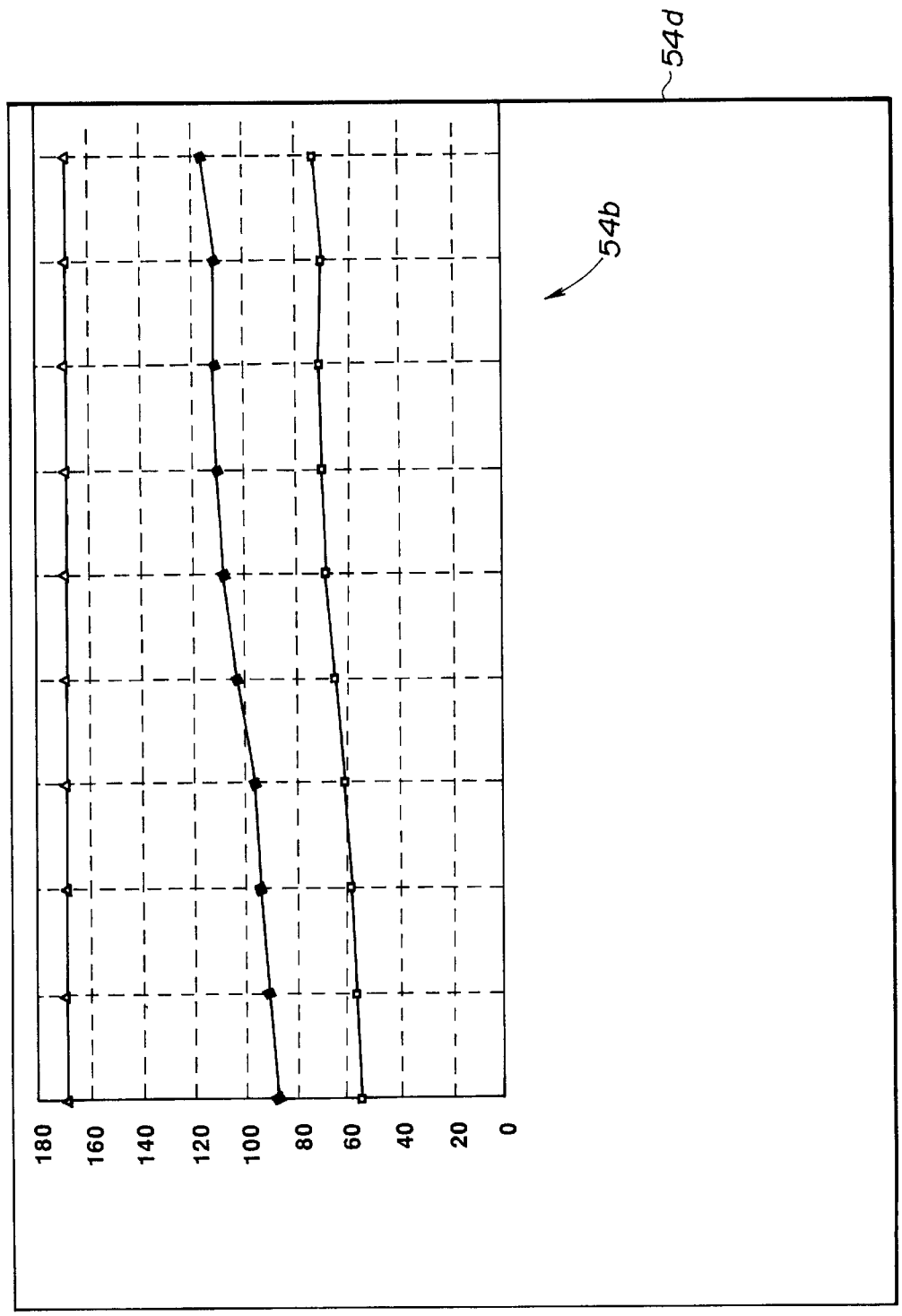

FIG. 14 shows the image data of the time-series graph which is stored in the graph storing area 54b. Time series is performed such that an inspection date is updated from the left-hand side to the right-hand side.

Figure 15:
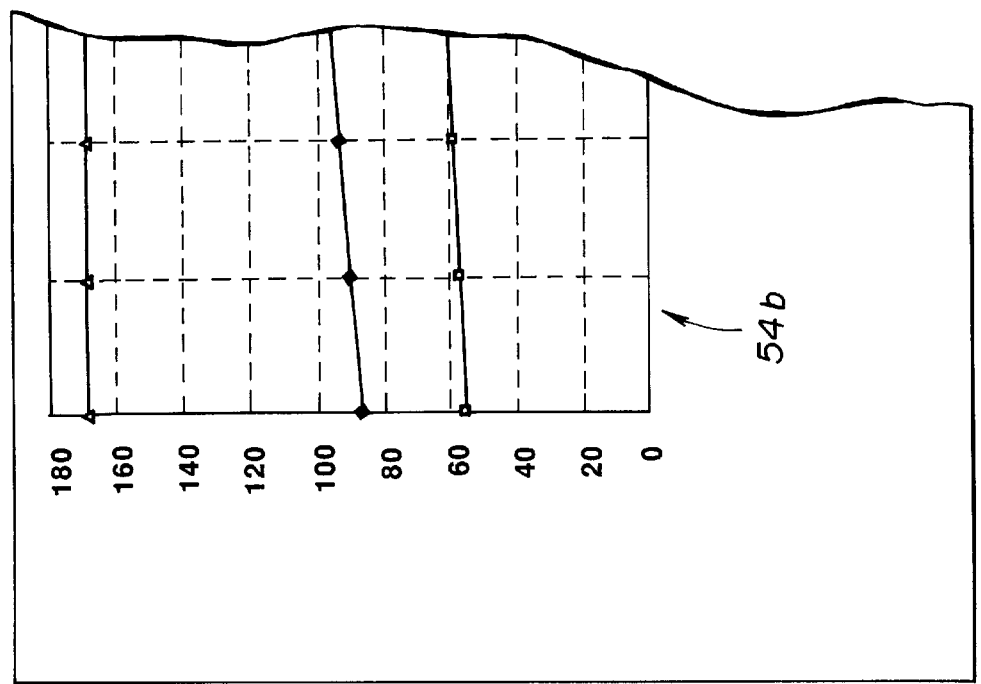
Figure 15:
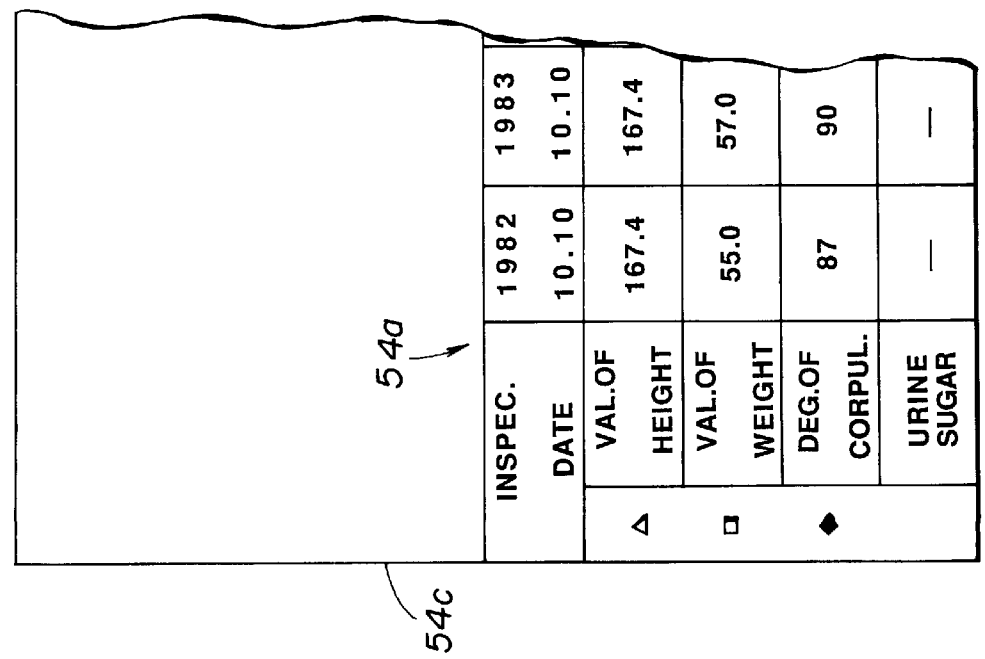

As shown in FIG. 15, the video RAM 54 comprises a pair of frame memories 54c and 54d. One of the frame memories 54c has an area on the lower side, which is used as the list storing area 54a. On the other hand, the other frame memory 54d has an area on the upper side, which is used as the graph storing area 54b. The respective storing areas are such that addresses are not overlapped with each other.

These frame memories 54*c* and 54*d* are such that common addresses are assigned, are simultaneously read out, are added to each other, and are converted to the standard image signal by the video-signal generating circuit 59, and a list and a graph are simultaneously displayed on the display 6 as indicated by the step S15.

In connection with the above, in a case where the data of the display item are not the numerical-value data, graphing is not performed with respect to the data, and the program proceeds to the step S16.

Figure 16:
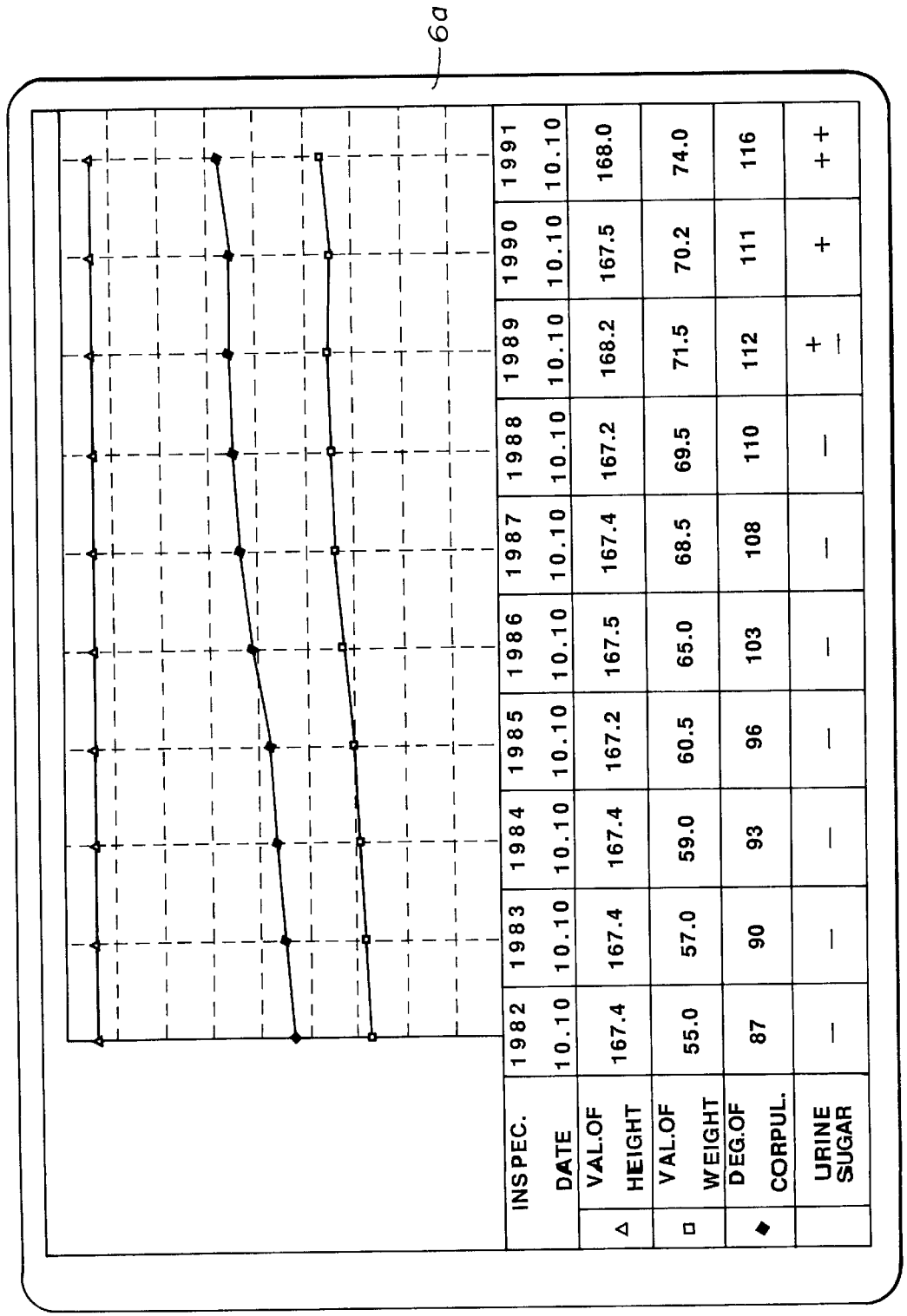

FIG. 16 shows the display surface 6*a* of the display 6 under a condition that the program is performed until the step S15. The time-series graph stored in the area on the upper side of the frame memory 54*d* is displayed on the upper side of the display surface 6*a*. The list of the data contents of the time-series items which are stored in the area of the frame memory 54*c* on the lower side is displayed on the lower side of the display surface 6*a*.

That is, the list of the data contents (the numerical values with respect to the items of the numerical-value data, and inclination or tendency or polarity with respect to the items of tendency and polarity) of the items selected in the time-series order and the graph of the time-series order with respect to the items having numerical-value data in these items are displayed simultaneously on the display surface 6*a*.

In other words, the list of the data contents of the selected items and the graph of the time-series order are displayed simultaneously on the same display surface 6*a*.

The list on the lower side of the display surface 6*a* arranges various inspection items including the height, the weight, the degree of corpulence and the urine sugar in a line direction, and displays the data of the inspection results corresponding to the inspection dates in a row direction.

The graph on the upper side of the display surface 6*a* displays that the corresponding inspection data are graphed with the axis of abscissa being the same as the inspection date of the display of the list, and with the axis of ordinates being inspection numerical values.

Of the display in the list illustrated in FIG. 16, the numerical-value data are the height, the weight, and the degree of corpulence. Accordingly, if the program is performed up to the step S15, a graph of broken line corresponding to the respective numerical-value data of the height, the weight and the degree of corpulence is displayed on the upper side of the display surfacer 6*a* in a time-series manner.

In the graph of broken line, points corresponding to the numerical-value data are such that the height is displayed by Δ, the weight is displayed by □ and the degree of corpulence is displayed by ♦, and the respective items and the marks are displayed on a column in the list at a lower portion of the image plane on the left end. Accordingly, it is made clear what graph corresponds to what inspection item. In this manner, the inspection data are graphed and are displayed, whereby variation in the inspection data can easily be grasped in a visual-sense manner.

In connection with the above, in a case where the numerical-value data are graphed, the magnitudes of the numerical values are generally different from each other every inspection items. Accordingly, the arrangement may be such that, in order to display them on the common display 6 so as to be easy to see, the CPU 51 normalizes the numerical-value data every inspection items and outputs the same, for example, and the axis of ordinates of the graph is displayed as a normalized common value, like the display example.

Furthermore, in a case where the data after normalization processing has, for example, been performed are graphed, the arrangement may be such that, in a case where a plurality of inspection data are superimposed upon each other, remarkable inspection data shift upwardly or downwardly, and can be displayed. The arrangement may also be such that, reversely, inspection data other than the remarkable inspection data shift upwardly or downwardly and can be displayed.

In order to end display illustrated in FIG. 16, Y or YES is inputted to the keyboard 5 in the step S16. In order to display another inspection item or items, N or NO is inputted to the keyboard 5.

Here, if the end of the display is selected, the computer 4 eliminates the display on the display 6 in a step S17, to emit the optical card 2 out of the optical-card reader/writer 3. On the other hand, if the display is not ended, and other inspection items are further displayed, the program is returned to the selection of the display items (step S9).

Subsequently, a case where guidance is performed by the display surface 6*a* illustrated in FIG. 16 will be described.

It can be grasped from the broken line graph at an upper portion of the display surface 6*a* in a visual-sense manner that, although the height is substantially constant, the weight and the degree of corpulence increase every year. Further, it can be confirmed as exact numeral values from the list on the lower portion of the display surface 6*a* that, in spite of the fact that the weight was 55.0 kg and the degree of corpulence was 87% on Oct. 10, 1982, the weight was 74.0 kg and the degree of corpulence was 116% on Oct. 10, 1991.

Moreover, it can be confirmed from the list on the lower portion of the display surface 6*a* that the urine sugar was ± on Oct. 10, 1989, was + on Oct. 10, 1990, and was ++ on Oct. 10, 1991.

From the information of the inspection results, a director or a leader such as a doctor or a health nurse can bring the information of the inspection results as reference materials of a diagnosis of diabetes mellitus, since a proprietor of the optical card 2 is such that urine sugar is detected in keeping with an increase in the weight and the degree of corpulence. Further, it is possible to explain the relationship between the weight and the degree of corpulence and the urine sugar to the proprietor of the optical card 2 by the list and the graph on the display surface 6*a* so as to be easily understood. Thus, it is also possible to urge self-management.

As described above, according to the present embodiment, the content data of the inspection item and the graph of the numerical-value data which are simultaneously selected are simultaneously displayed on the same display surface 6*a*, whereby it is possible to grasp variation of data of a plurality of associated items by simple operation in a visual-sense manner from the same display surface 6*a*, and it is possible to know exact numerical values with respect to the numerical-value data in the data of the various inspection items without switching of the display surface 6*a*.

For the reason described above, there can be produced materials for performing adequate advice, guidance and the like with respect to the proprietor of the optical card 2 from the list and the graph displayed on the display surface 6*a* without switching of the display contents.

Further, since the list of the data and the graph of the numerical-value data relating to a plurality of inspection items associated with the single display surface 6*a* can be displayed, it is possible to totally check data from the single display surface 6*a*.

In connection with the above, in the first embodiment, it has been described that, in a case where the numerical-value data are displayed in the graph, the numerical-value data are displayed by the broken line graph. However, the invention should not be limited to this specific arrangement. For example, the numerical-value data may be displayed by a bar graph and other graphs, for example. Moreover, the display 6 may use a display such as a CRT, a liquid crystal, or the like, or may be a printer. Furthermore, a recording unit of the information outputted to the display 6 may be provided.

In connection with the above, in display of the inspection data, displayed inspection data may further be added or may further be deleted, with respect to the condition displayed as shown, for example, in FIG. 16. Furthermore, such function may be provided that the data on the display surface 6a are used so that a rate or a ratio of time-series variation can be computed or displayed.

Figure 17:
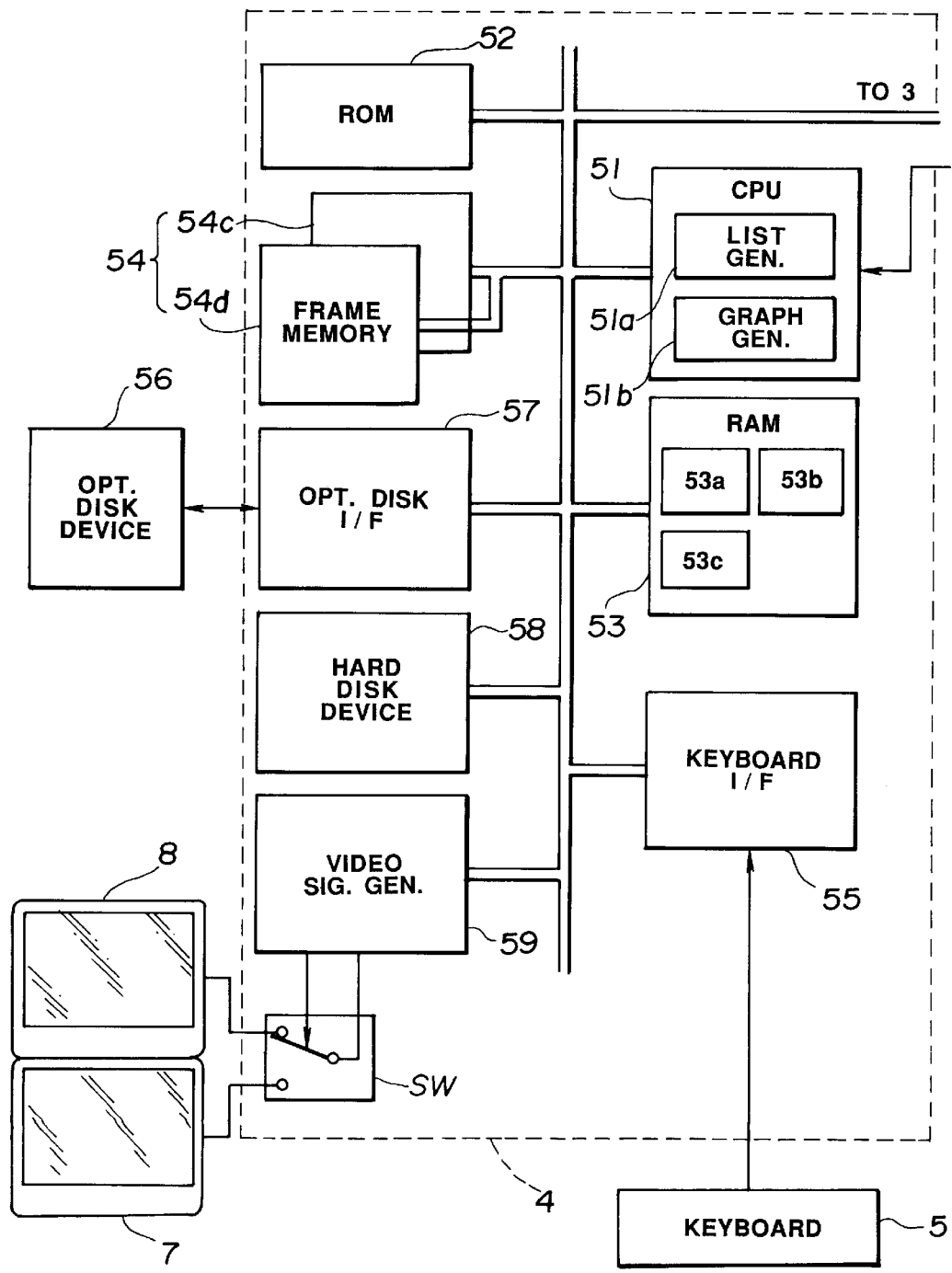
FIGS. 17 and 18 relate to a second embodiment of the invention, FIG. 17 being a block diagram showing an arrangement of a computer in the second embodiment.

FIG. 17 shows a principal portion in a second embodiment of the invention. In the second embodiment, a pair of display monitors 7 and 8 are provided in place of the display 6 shown in FIG. 6, a list in the time-series order is displayed on one of the monitors 7, and a graph of the time-series order is displayed on the other display monitor 8.

Further, in the present embodiment, backup recording means is provided for backing-up information recorded on an optical card 2. That is, an optical-disk device 56 is connected to a computer 4 through an optical-disk device I/F 57 so that information recorded on the optical card 2 is backed up.

The inspection data on all the inspecting dates are recorded on the optical disk device 56 every personal information on the optical card 2. In a case where inspection is performed with respect to a proprietor of the optical card 2, data with respect to all the inspection items performed on the inspection date are recorded on the optical card 2, and the data are recorded also on the optical disk device 56, to back-up the information recorded on the optical card 2.

In a case where inspection is performed, if the proprietor does not take the optical card 2, the inspection data of the date are recorded only on the optical disk device 56. Upon a chance or opportunity that the optical card 2 is taken, in a case or the like where the optical card 2 is inserted into an optical-card reader/writer 3, the backed-up information can be recorded onto the optical card 2 as shown in FIG. 18.

Further, in the present embodiment, the image data of the list of the time-series order data and the image data of the graph of the numerical-value data of the time-series order are stored respectively in two frame memories 54c and 54d which form the video RAM, similarly to the first embodiment. In this connection, differentiated from the first embodiment, the two storing areas may be such that addresses are caused to overlap each other.

Reading-out of the frame memories 54c and 54d is performed alternatively, passes through a video-signal generating circuit 59 and an analog switch SW, and is alternatively outputted to the monitors 7 and 8 at a cycle of one field of $\frac{1}{60}$ sec, for example. A switching signal of cycle of $\frac{1}{30}$ sec generated by the use of a vertical synchronous signal from the video-signal generating circuit 59 is applied to the analog switch SW.

Figure 7:
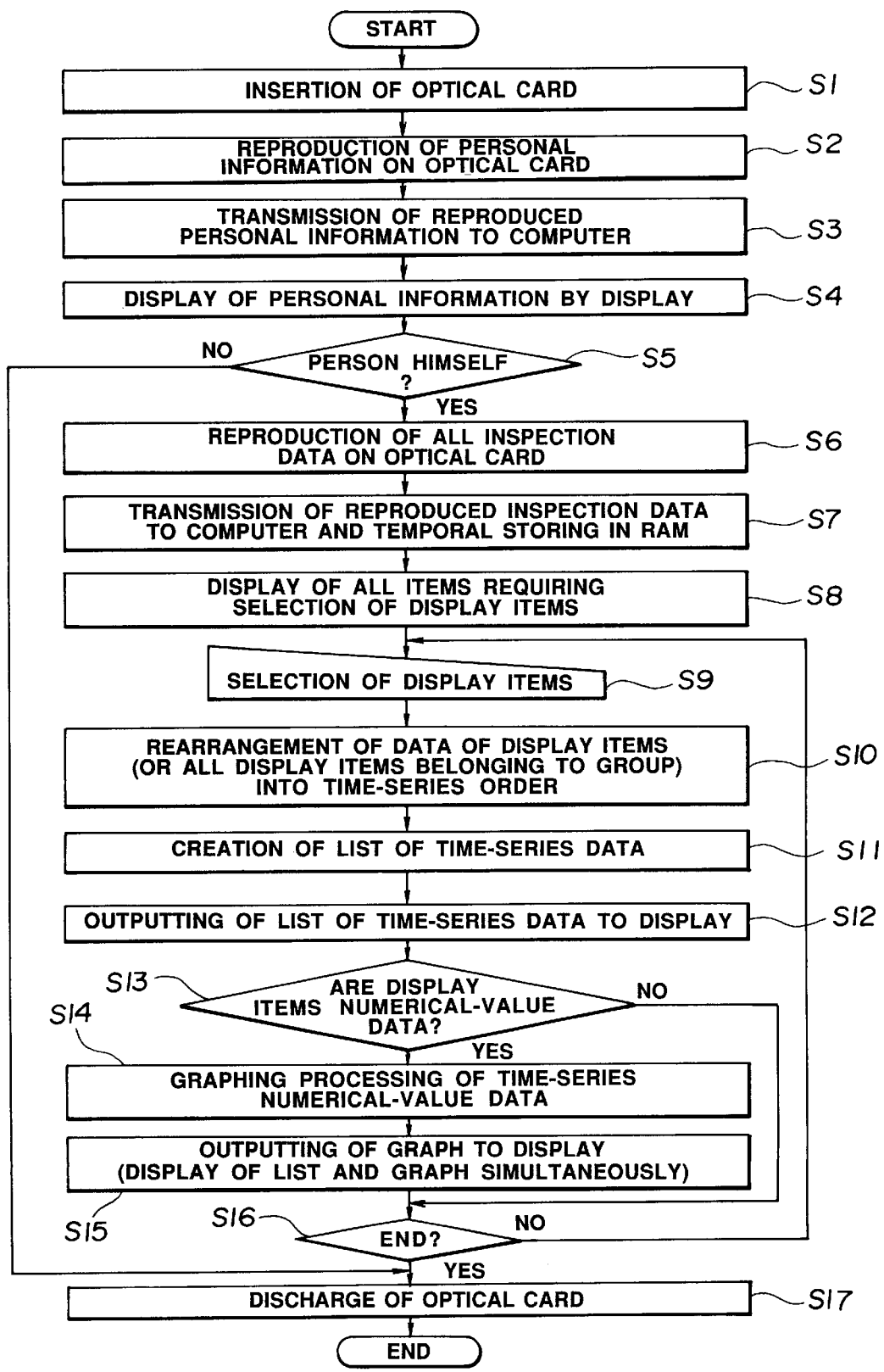
Figure 18:
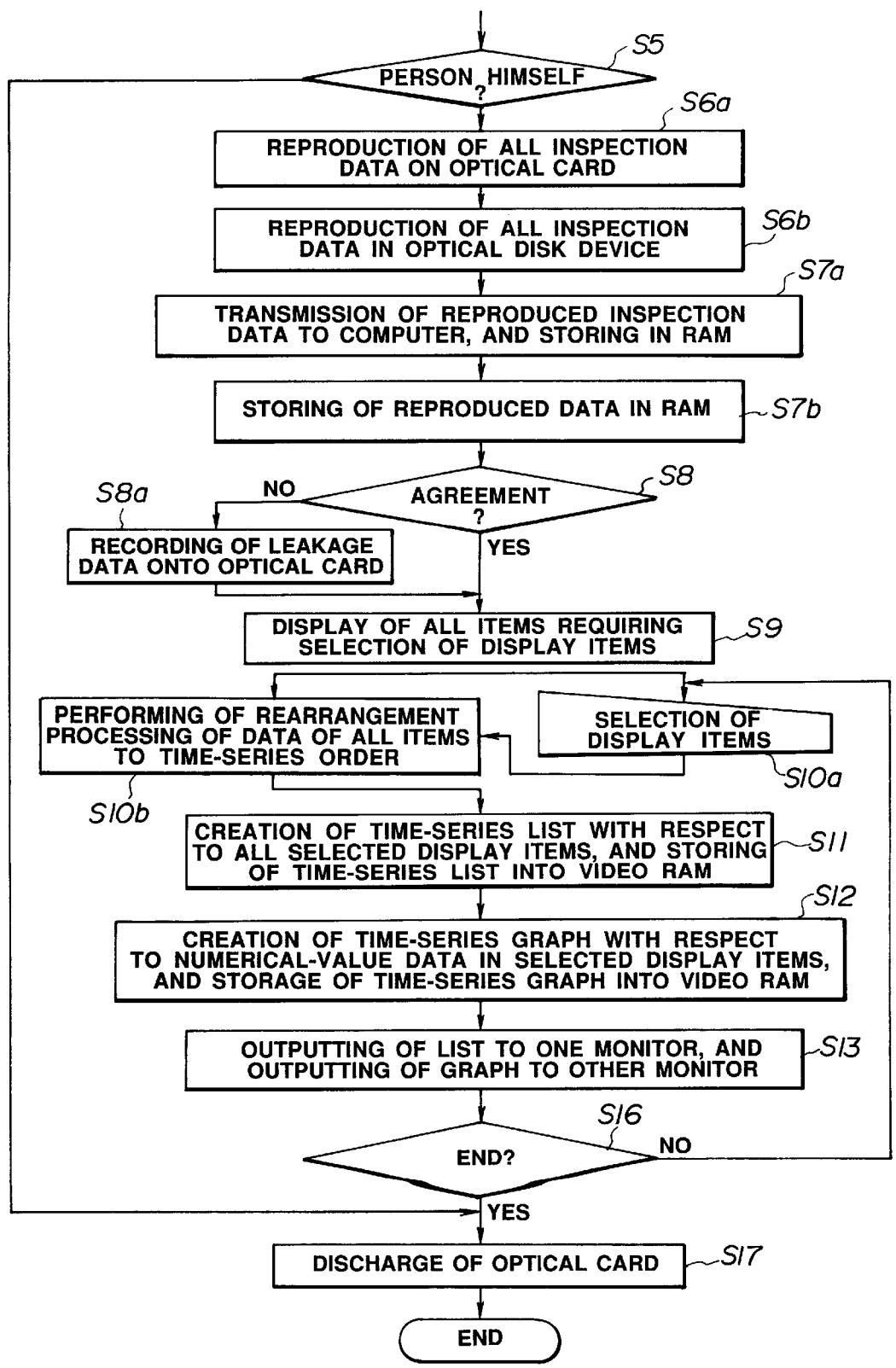

In FIG. 18, in a case where the optical card 2 is inserted into the optical-card reader/writer 3, the program is the same as that illustrated in FIG. 7 up to a step S5.

In a case where it is confirmed in the step 5 that the person is the person himself, all the inspection data are reproduced from the optical card 2 by the optical-card reader/writer 3 (step S6a). Further, the optical disk device 56 uses the personal information (step S3) to reproduce all the inspection data corresponding to the personal information (step S6a).

The inspection data reproduced respectively are stored in reproduced-data storing areas 53a and 53a' of the RAM 53 (step S7a and step S7b).

In a subsequent step S8, it is Judged whether or not the two inspection data stored in the reproduced-data storing areas 53a and 53a' are coincident with each other (that is, in the data reproduced from the optical card 2, whether or not there exist the inspection data of the inspecting data which are not recorded, with respect to the backed-up data). In a case where there exist no data which are not recorded, the program proceeds to a subsequent step S9.

In a case where there exist data which are not recorded, all the inspection data (referred also to as "leakage data") of the inspection date which is not recorded are recorded with respect to the optical card 2 which is inserted into the optical-card reader/writer 3 as indicated by a step S8a are recorded, and the program proceeds to the subsequent step S9.

In the step S9, a menu requesting selection of the display items is displayed. In a subsequent step S10a, an operator waits key inputting which performs selection of the display items. As indicated in a step S10b, processing is performed in which all the item data stored in the reproduced-data storing area 53a' are rearranged in time-series order. In a case where there is key inputting of selection during the processing of rearrangement, the key inputting is received at interruption and, subsequently, the rearrangement processing continues.

In a subsequent step S11, data of display items selected from all the data of items rearranged in the time-series order are extracted, to generate a time-series list. In this case, since the extracted data of the display items are data of time-series order in which rearrangement has already been ended, a ruled line and the like are drawn to generate a list which is stored in one of frame memories 54c which form a video RAM 54.

Further, a graph is generated from the numerical-value data, with respect to the items of the numerical-value data in the selected display items, and is stored in one of the frame memories 54d which form the video RAM 54 (step S12).

The image data of the list stored in the frame memory 54c of the video RAM 54 are outputted to one of the monitors 7, and the image data of the graph stored in the frame memory 54d are outputted to the other monitor 8.

In this case, the two monitors 7 and 8 do not strictly display the list and the graph simultaneously, but displays the same simultaneously by afterimage characteristic (for example, longer than $\frac{1}{60}$ sec) of the monitors 7 and 8. Moreover, also in a case where a doctor, a health nurse or the like observes the list and the graph, the list and the graph are observed as being displayed simultaneously from characteristic of eyes. Processing after a step 13 is the same as that illustrated in FIG. 7.

According to the second embodiment, the list of the time-series order data is displayed on the display surface 7a of the display monitor 7, and the graph is displayed on the display surface 8a of the display monitor 8. Accordingly, it is made possible to increase the size of the display to display the list and the graph under such a condition as to see or look and in a more detailed manner.

Furthermore, even if there is recording leakage in the optical card 2, it is possible to use the backed-up data to refer to all the inspection data including data of recording leakage, to thereby use the recording leakage as materials for guidance and advice. For this reason, more adequate guidance and advice are made possible.

In the first and second embodiments, the predetermined group is selected whereby the list of the data of all the items belonging to the group and the graph of all the numerical-value data (with respect to the items of the numerical-value data) are displayed simultaneously. However, the arrangement may be such that a plurality of items desired to be displayed are freely selected, and a list of data of a selected plurality of items and a graph of numerical-value data in a case of the items of the numerical-value data are displayed simultaneously.

Figure 19:
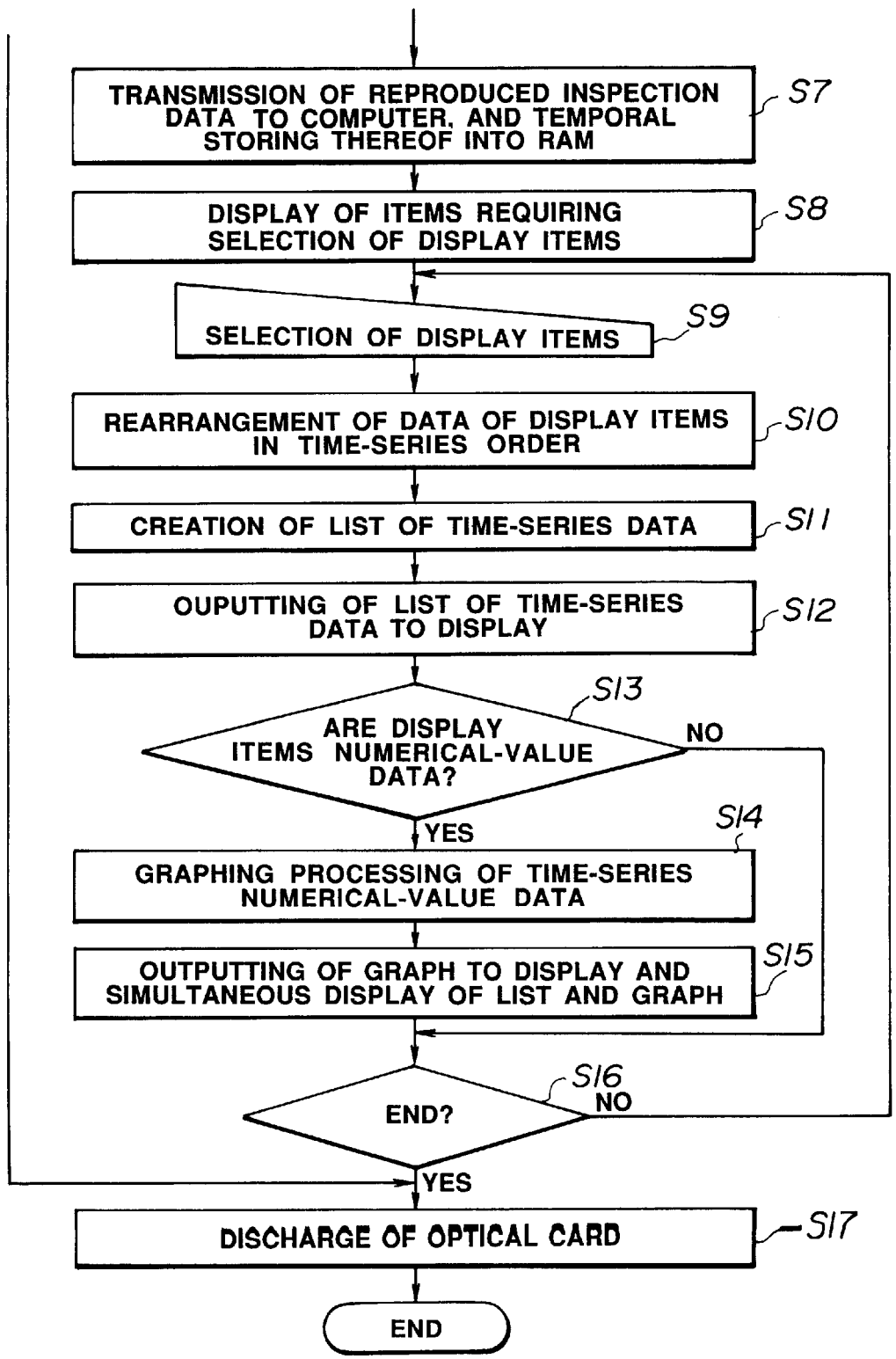

FIG. 19 shows processing operation of a third embodiment. A program is the same as that illustrated in FIG. 7 up to a step S7. A subsequent step S8 is substantially the same as that shown in FIG. 7, but menus of selection in this case are brought to ones illustrated in FIG. 20. That is, in a menu shown in FIG. 10, only a list of simple items is displayed. In this case, it is possible to select a plurality of optional items. Selection of display items is performed by a subsequent step S9.

For example, FIG. 20 shows a condition in which the numbers of a degree of corpulence, urine protein, urine occult blood and urine sugar, that is, 3, 6, 7 and 8 are selected.

Figure 21:
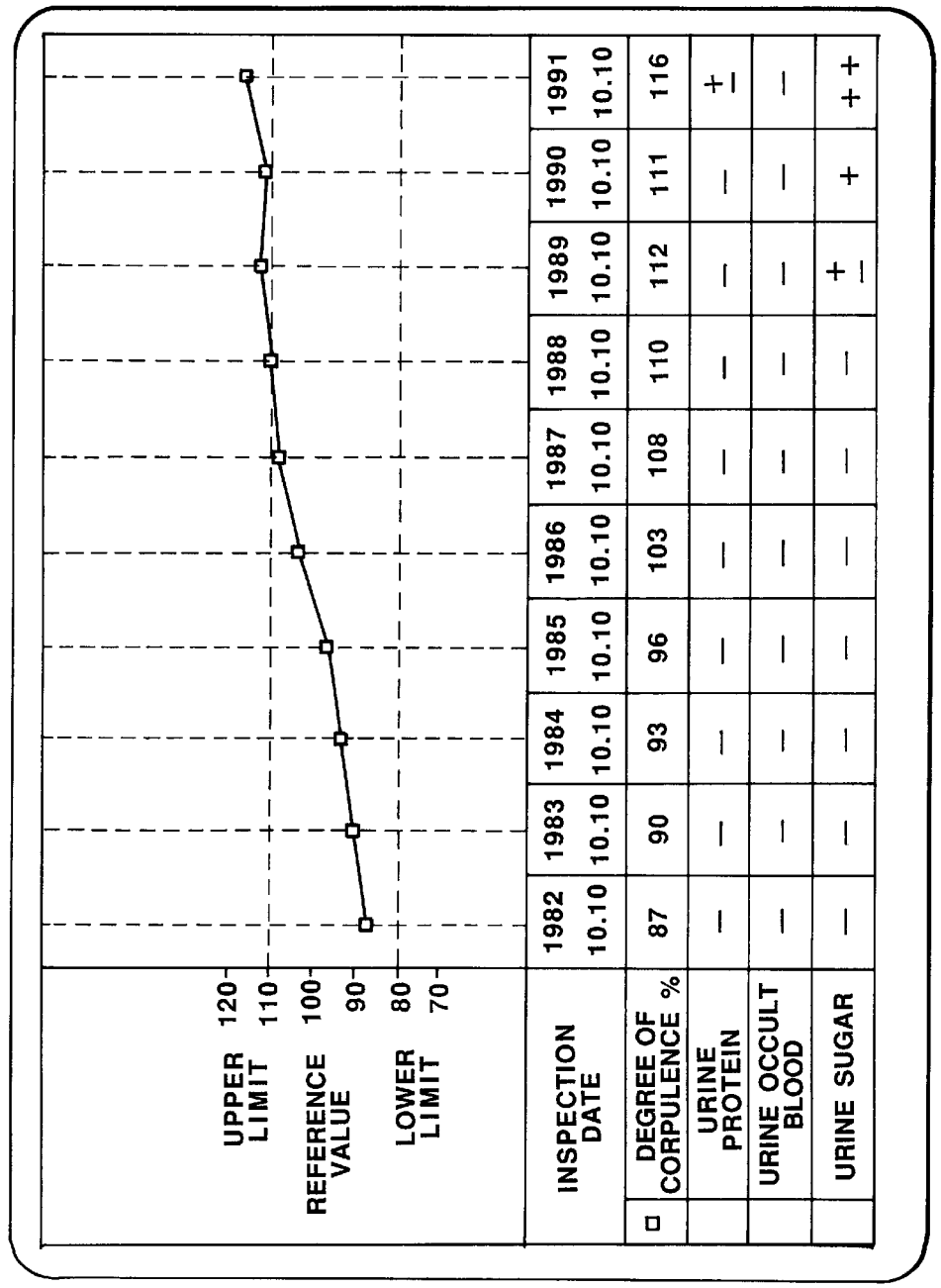

Then, in a step S10, rearrangement of data of the selected display items is performed. Similarly to FIG. 7, the list and the graph are displayed simultaneously on the display 6 by steps S11~S15, as shown in FIG. 21. In this display, the items different from those of the first embodiment are selected. Accordingly, although the embodiment in FIG. 16 is different from the embodiment in FIG. 19, the embodiment in FIG. 16 and the embodiment in FIG. 19 are the same as each other in that the list and the graph are displayed simultaneously. Steps subsequent to a step S16 are also similar to those shown in FIG. 7.

Of the display of the list illustrated in FIG. 21, the numerical-value data are only the degree of corpulence. Accordingly, if the step S15 is performed, a graph of broken line which connects □ of mark corresponding to the numerical-value data of the degree of corpulence is displayed in time series on an upper portion of an image plane. In four (4) inspection items selected, in a case where inspection data are a plurality of numerical-value data, marks different from each other correspond. By a graph of broken line connecting the marks different from each other, to each other, graphs of numerical-value data of various inspection items are distinguished from each other, and various tendencies or inclinations are understood in a visual sense manner.

In connection with the above, in the first embodiment, for example, it has been described that, in the step S7 in FIG. 7, the inspection data reproduced are transmitted to the computer 4 and, thereafter, the display items are selected. However, the arrangement may be such that the display items are previously selected and, thereafter, the Inspection data of the selected item are reproduced and are transmitted to the computer 4. Further, in a case where the inspection data are reproduced and are transmitted to the computer 4, the arrangement may be such that only the inspection data of the selected item are transmitted to the computer 4.

In connection with the above, various groups of the preset inspection items have been stored in the computer 4. However, the arrangement may be such that groups of specific inspection items are set in the optical card 2 used and are recorded thereon, and, in a case where the display items are selected, the display items are read out of the optical card 2 so that the display items are selectable. By doing so, it is possible to easily perform changing of a plurality of items selected by a proprietor of the optical card 2 are changed. Thus, efficient guidance is made possible.

Moreover, the various groups of the selected inspection items have been preset. However, the arrangement may be such that the contents of the recording means within the computer 4 or the data within the optical card 2 are rewritten so that the groups of inspection items can be changed or groups can newly be added.

Furthermore, the various embodiments have been described by the use of the optical card as the information recording medium. However, the various embodiments can be applied also to recording media such as IC cards, floppy disks and the like.

Further, the various embodiments have been described regarding the example of use in the medical treatment field of art. However, the information in the embodiments may be inspection hysteresis information of articles, and information other than the inspection hysteresis information.

As described above, according to the present invention, there are produced advantages that variation of the inspection data of the plurality of inspection items can be grasped in a visual sense manner by simple operation, and exact numerical values of the various inspection items can be known without switching of the display surface.

In connection with the above, it is possible that the above-described embodiments or the like are combined with each other partially or the like to form different embodiments. These different embodiments belong to the present invention.

What is claimed is:

1. An information display system, comprising:
    reproducing means for reproducing information regarding a plurality of items recorded onto information recording media;
    selecting means for selecting combined item groups which are grouped into a plurality of predetermined combinations of items, among information regarding the plurality of items reproduced by said reproducing means;
    time-series order numerical-value data generating means for generating time-series order numerical-value data in which numerical-value data are brought into said time-series order, which respect to items including said numerical-value data, and belonging to the combined item groups selected by said selecting means;
    time series order graph generating means for generating a time-series order graph in which said numerical-value data are graphed in said time-series order, with respect to items including said numerical-value data; and
    display means for displaying simultaneously said time-series order numerical-value data and said time-series order graph on a single screen of the display means.

2. An information display system according to claim 1, wherein each of said information recording media consists of an optical card in which reproduction of the information is optically performed.

3. An information display system according to claim 1, wherein said reproducing means comprises an optical reproducing means for performing reproduction of information recorded on said information recording media by the use of an optical beam.

4. An information display system according to claim 1, wherein said display means further displays a name of the items including said numerical-value data.

5. An information display system according to claim 1, wherein said information recording media record the information extending over said plurality of items by a time-series unit.

6. An information display system according to claim 1, wherein said information recording media record the information extending over said plurality of items, together with identification information which identifies said items.

7. An information display system according to claim 6, wherein said identification information is number information corresponding to said items.

8. An information display system according to claim 1, wherein said time-series order numerical-value data generating means forms combined items which are selected by said selecting means, and generates time-series order polarity/tendency data in which said polarity/tendency data are brought to time-series order, with respect to the items having polarity/tendency data which indicate one of polarity and tendency.

9. An information display system according to claim 8, wherein said display means displays time-series order polarity/tendency data, together with said time-series order numerical-value data.

10. An information display system according to claim 1, wherein said display means displays said time-series order numerical-value data by a list which includes ruled lines.

11. An information display system according to claim 1, including memory means which temporarily stores said time-series order numerical-value data which are generated by said time-series order numerical-value data generating means, and the image data of said time-series order graph generated by said time-series order graph generating means.

12. An information display system according to claim 1, wherein whenever the combined items selected by said selecting means are items including a plurality of numerical-value data, said display means simultaneously displays a plurality of time-series graphs which correspond to said plurality of numerical-value data.

13. An information display system according to claim 1, wherein said time-series order numerical-value data generating means generates time-series order numerical-value data with respect also to items other than the items which belong to the combined items selected by said selecting means.

14. An information display system according to claim 1, wherein said time-series order numerical-value data generating means generates time-series order polarity/tendency data in which said polarity/tendency data are brought to time-series order, with respect to the items having polarity/tendency data which indicate one of polarity and tendency, other than the items which belong to the combined items selected by said selecting means.

15. An information display system according to claim 1 wherein said display means includes first display means for displaying said time-series order numerical-value data, and second display means for displaying said time-series order graph.

16. An information display system according to claim 1, wherein said reproducing means includes a recording function which records information onto said information recording media.

17. An information display system according to claim 1, including a backup recording unit for backup-recording information recorded onto said information recording media.

18. An information display system according to claim 17, including a detecting function for detecting recording leakage in the recording information which is recorded onto said information recording media with respect to backup information which is recorded on said backup recording unit.

19. An information display system according to claim 18, including a recording means for recording said recording leakage information onto said information recording media, in a case where said recording leakage is detected.

20. An information display system according to claim 1, wherein said selecting means consists of a keyboard.

21. An information display system comprising:

reproducing means for reproducing information regarding a plurality of items which are recorded onto information recording media;

selecting means for selecting combined item groups grouped into predetermined combinations of said plurality of items, among information regarding the plurality of items which are reproduced by said reproducing means;

time-series order data generating means for generating time-series order data in which numerical-value data are brought into said time-series order, with respect to items including said numerical-value data and belonging to groups of combined item groups selected by said selecting means;

time-series order graph generating means for generating a time-series order graph in which said numerical-value data are graphed in said time-series order, with respect to items including said numerical-value data; and display means for displaying said time-series order data and said time-series order graph within the same display surface so that said time-series order data and said time-series order graph can be viewed simultaneously.

22. An information display system comprising:

reproducing means for reproducing information regarding a plurality of items which are recorded onto information recording media;

selecting means for selecting a plurality of items from among information regarding the plurality of items reproduced by said reproducing means;

time-series order data generating means for generating time-series order data in which numerical-value data are brought into said time-series order, with respect to items including said numerical-value data and forming a plurality of items selected by said selecting means;

time-series order graph generating means for generating a time-series order graph in which said numerical-value data are graphed in said time-series order, with respect to items including said numerical-value data; and display means for combining said time-series order data and said time-series order graph on a single screen of the display means so as to be capable of being viewed simultaneously.

* * * * *